US011023841B2

(12) United States Patent
Bradbury et al.

(10) Patent No.: US 11,023,841 B2
(45) Date of Patent: Jun. 1, 2021

(54) WORKSITE RISK ANALYSIS AND DOCUMENTATION SYSTEM AND METHOD

(71) Applicants: Samuel Bradbury, Santa Fe, NM (US); Mark Heidebrecht, Olathe, KS (US)

(72) Inventors: Samuel Bradbury, Santa Fe, NM (US); Mark Heidebrecht, Olathe, KS (US)

(73) Assignee: Ergonomics International, LLC, Olathe, KS (US)

( * ) Notice: Subject to any disclaimer, the term of this patent is extended or adjusted under 35 U.S.C. 154(b) by 810 days.

(21) Appl. No.: 15/871,810

(22) Filed: Jan. 15, 2018

(65) Prior Publication Data

US 2018/0204155 A1 Jul. 19, 2018

Related U.S. Application Data

(60) Provisional application No. 62/446,843, filed on Jan. 17, 2017.

(51) Int. Cl.
| | |
|---|---|
| *G06K 9/00* | (2006.01) |
| *G06Q 10/06* | (2012.01) |
| *G06K 9/20* | (2006.01) |
| *G06T 7/20* | (2017.01) |
| *G16H 50/30* | (2018.01) |
| *A61B 5/11* | (2006.01) |

(52) U.S. Cl.
CPC ............ *G06Q 10/0635* (2013.01); *A61B 5/11* (2013.01); *G06K 9/00342* (2013.01); *G06K 9/00711* (2013.01); *G06K 9/20* (2013.01); *G06Q 10/0631* (2013.01); *G06Q 10/0637* (2013.01); *G06T 7/20* (2013.01); *G16H 50/30* (2018.01)

(58) Field of Classification Search
CPC .. G06K 9/20; G06K 9/00342; G06K 9/00711; G06Q 10/0631; G06Q 10/0635; G06Q 10/0637; A61B 5/11; G06T 7/20; G16H 50/30

See application file for complete search history.

(56) References Cited

U.S. PATENT DOCUMENTS

| | | | | |
|---|---|---|---|---|
| 8,370,170 | B2 * | 2/2013 | Legge | A61B 5/1116 705/2 |
| 8,631,161 | B2 * | 1/2014 | Lavrov | G06Q 10/063114 709/248 |
| 10,672,089 | B2 * | 6/2020 | Howe | G06Q 50/163 |
| 2003/0069716 | A1 * | 4/2003 | Martinez | G06Q 10/06 702/188 |
| 2004/0236598 | A1 * | 11/2004 | Thomsen | G06Q 10/10 705/321 |
| 2014/0006060 | A1 * | 1/2014 | Sehnal | G06Q 10/0631 705/4 |

* cited by examiner

*Primary Examiner* — Tom Y Lu
(74) *Attorney, Agent, or Firm* — Christopher Pilling

(57) ABSTRACT

A worksite risk analysis and documentation system and method defines, captures, categorizing, and documents, while analyzing functional physical demands of a plurality of jobs at various worksites, including environmental health and safety risks/opportunities as well as ergonomic risks/opportunities. The system and method prioritizes risk and body part injury based on individual injury costs associated with each body part used in various tasks at the worksite. The system and method creates a report which includes a catalog of engineered solutions and administrative control solutions to various issues and ergonomic risks/opportunities.

17 Claims, 33 Drawing Sheets

FIG. 4

*What are the tasks that contribute the most to the difficulty and fatigue of performing this job?*

| | Task Name | Task Name | Task Name | Task Name |
|---|---|---|---|---|
| Step 1 - Task Name | Setup | Loading | Mixing | Clean up |
| Step 2 - Frequency | Every Day | Every Day | Every Hour | Every Day |
| | 2 | 2 | 2 | 2 |

*What is the most critical factor that makes the job task fatiguing or difficult?*

| | Rate the Difficulty/Fatigue | Rate the Difficulty/Fatigue | Rate the Difficulty/Fatigue | Rate the Difficulty/Fatigue |
|---|---|---|---|---|
| Step 3 - Rate the task difficulty | 3 | 7 | 2 | 4 |
| | Setup | Loading | Mixing | Clean up |

*What is the most critical factor that makes the job task fatiguing or difficult?*

| | What is the most critical factor that makes the job task of fatiguing or difficult? | What is the most critical factor that makes the job task fatiguing or difficult? | What is the most critical factor that makes the job task fatiguing or difficult? | What is the most critical factor that makes the job task fatiguing or difficult? |
|---|---|---|---|---|
| | Setup | Loading | Mixing | Clean up |
| Step 4 - Reason for difficulty | Posture or Position | Posture or Position | Obstacles or Obstructions | Environmental Factors |
| | Obstacles or Obstructions | Obstacles or Obstructions | | |
| | Frequency or Repetitions | Force or Weight | | |
| | Contact Stress | | | |
| | Vibration | | | |
| | Environmental Factors | | | |

| Body Part | Observations | Right | Left | Answer |
|---|---|---|---|---|
| Back | Lifting more than 30 lbs below the knees | | | No |
| Back | Lifting more than 50 lbs | | | No |
| Back | Greater than 1 lift per minute | | | No |
| Back | Carrying more than 50 lbs both hands | | | No |
| Back | Carrying more than 25 lbs single hands | | | No |
| Back | Twisting with weight | | | No |
| Back | Bending torso greater than 60 degrees forward | | | No |
| Back/Shoulder | Lifting more than 20 lbs above the shoulder | | | No |
| Back/Shoulder | Pushing or pulling with a force more than 40 lbs 2 hands | | | No |
| Back/Shoulder | Pushing or pulling with a force more than 20 lbs 1 hand | No | Yes | Yes |
| Shoulder | Reaching beyond 20 in. in any direction | Yes | Yes | Yes |
| Shoulder | Reaching above, or elbow above the shoulder | Yes | Yes | Yes |
| Shoulder | Reaching behind, or elbow behind the shoulder | Yes | Yes | Yes |
| Shoulder | Reaching across the body or to the side of the body | Yes | Yes | Yes |
| Shoulder | 3 or more reaches per minute | Yes | Yes | Yes |
| Shoulder | Rotating upper arm (rotator cuff movement) | Yes | Yes | Yes |
| Shoulder | Throwing product to perform their job | Yes | Yes | Yes |
| Shoulder/Neck | Sustained shoulder shrugging | Yes | Yes | Yes |
| Forearm/Shoulder | Lifting (bicep curl) 10 or more reps per minute | No | No | Yes |
| Forearm | Lifting (bicep curl) greater than 20lbs | No | No | Yes |
| Forearm | 10 or more forearm movements per minute (screwdriver) | No | No | Yes |
| Forearm | Palm up and exerting force | No | No | Yes |
| Hand | 30 or more repetitive wrist motions per minute | No | No | Yes |
| Hand | 15 or more hand grasp or pinch motions a minute | No | No | Yes |
| Hand | 200 or more finger movements per minute | No | No | Yes |
| Hand | Pinching or gripping with force | No | Yes | Yes |
| Hand | Awkward Posture of the wrist | No | Yes | Yes |
| Hand | Hand use required in cold environment | No | Yes | Yes |
| Hand/Neck | Repetitive precision tasks | No | Yes | Yes |
| Neck | Sustained head or neck posture in awkward position | No | Yes | Yes |
| Neck | Use of hard had or faceshield | No | Yes | Yes |
| Neck | Frequent/repetitive head movements | No | Yes | Yes |

Task Name
Severity

| Likelihood | Insignificant 1 | 2 | 3 | 4 | 5 | 6 | 7 | 8 | 9 | Catastrophe 10 |
|---|---|---|---|---|---|---|---|---|---|---|
| 10 | 10 | 20 | 30 | 40 | 50 | 60 | 70 | 80 | 90 | 100 |
| 9 | 9 | 18 | 27 | 36 | 45 | 54 | 63 | 72 | 81 | 90 |
| 8 | 8 | 16 | 24 | 32 | 40 | 48 | 56 | 64 | 72 | 80 |
| 7 | 7 | 14 | 21 | 28 | 35 | 42 | 49 | 56 | 63 | 70 |
| 6 | 6 | 12 | 18 | 24 | 30 | 36 | 42 | 48 | 54 | 60 |
| 5 | 5 | 10 | 15 | 20 | 25 | 30 | 35 | 40 | 45 | 50 |
| 4 | 4 | 8 | 12 | 16 | 20 | 24 | 28 | 32 | 36 | 40 |
| 3 | 3 | 6 | 9 | 12 | 15 | 18 | 21 | 24 | 27 | 30 |
| 2 | 2 | 4 | 6 | 8 | 10 | 12 | 14 | 16 | 18 | 20 |
| 1 | 1 | 2 | 3 | 4 | 5 | 6 | 7 | 8 | 9 | 10 |

| | Hand | | Forearm | | Hand/ Neck | Neck/Hand | | Shoulder/ Neck | | Shoulder/Neck | | Back/ shoulder | Shoulder | | Shoulder |
|---|---|---|---|---|---|---|---|---|---|---|---|---|---|---|---|
| | Right | Left | Right | Left | Neck | Right | Left | Neck | Back | Right | Left | shoulder | Right | | Left |
| 1 | 0 | 30 | 0 | 0 | 0 | 0 | 58 | 0 | 80 | 50 | 50 | 0 | 90 | 80 | 90 |
| | 1 | 2 | 3 | 4 | 5 | | | 6 | 7 | | | 8 | 9 | | 10 |

Severity is established
Likelihood is exposure + number performing task
Likelihood =(exposure * number of man hours worked)/number workers performing task
Perception of difficulty Probability/Severity Score Body Part Score
171

FIG. 8A

TASK SPECIFIC TEST PROTOCOL

*Inclined surface lift*

Test Instructions:

*Follow the test instructions and sequence in the Actitivities and Special Instructions section below.*

Complete the test pictured below as per the requirements listed on the front page. Follow the reps, load, frequency rate, and time requirements for completion of the task.

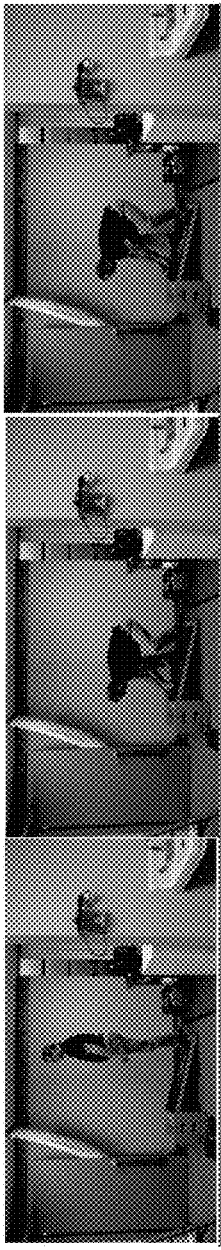

| Functional Test | Force | Reps or Time Requirement | Activities and Special Instructions |
|---|---|---|---|
| Inclined surface lift | 20 lbs | 4 reps per side | Establish testing position and equipment layout as shown in photos below. Stand at end of incline board.<br>Step, squat, kneel and lift plate to the individual's chest level. Set weight down. Release and repeat. Weight should be 20 pound plate weight. The distance between plate start point and plate finish point is established at 12 inches in front of subject. Weight is lifted from the inclinde surface to waist level every 15 seconds. Activity is completed over 3 minutes. |

*Review and confirm the following for the test:*

The applicant was able to keep up with the timing required to complete the task.
The applicant was able to complete the repetitions required.
The applicant was able to maintain grip or grasp on the lifted object throughout testing and did NOT need to rest?
Excessive substitution patterns such as jerking, swaying, thrusting or shrugging were NOT observed.
Alternative body movements were NOT observed during the task (i.e swaying or rocking).
Excessive upper trap, cervical, or trunk muscular engagement were NOT used to complete task.
Excessive heavy breathing, profuse sweating, or flushing of the face were not present at the end of the test.
Applicant had no complaints of discomfort or pain during or after test.
Fatigue symptoms were NOT observed.
Ability to assume and maintain the required work posture was observed to be consistent with required work.

Notes:

FIG. 8B

Grip Testing
*Single Hand Grip*

Test Instructions:

*Neutral:* *Grip dynamometer set to position 3. Dominant hand is noted. Testing is completed in a seated or standing position with arm to be tested in a 90 degree angle at the elbow and arm to side. Grip is initiated and sustained until tester says "stop". Individual should be able to generate a static force of required a minimum of the required repetitions consecutively.*

*Posture Specific:* *See special instructions section.*

Complete the test pictured below as per the requirements listed on the front page. Follow the reps, load, frequency rate, and time requirements for completion of the task.

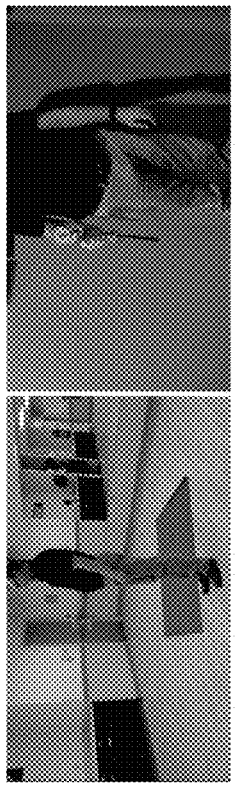

| Lifting | Force in lbs or kg | Repetitions Required | Neutral | Posture Specific | Special Instructions |
|---|---|---|---|---|---|
| Static Single Hand Grip 1 | 40 lbs | 3 time | Position 2 | N/A | |
| Endurance Grip | 15 lbs | 1 time every 15 sec | Position 2 | N/A | |
| Static Single Hand Grip 2 | 35 lbs | 1 min during test | Position 2 | N/A | |
| Positional Grip | N/A | N/A | N/A | N/A | |

*Review and confirm the following for the test:*

The applicant was NOT able consistently meet the grip level required.
The applicant was able to keep up with the timing required to complete the task.
The applicant was able to complete the repetitions required.
Excessive substitution patterns such as elbow, shoulder, neck or grimacing were NOT observed.
Excessive upper trap, cervical, or trunk muscular engagement were NOT used to complete task.
Excessive heavy breathing, profuse sweating, or flushing of the face were not present at the end of the test.
Applicant had no complaints of discomfort or pain during or after test.
Rubbing of the wrist, hand or fingers were NOT observed.

Notes:

FIG. 8C

CARRY PROTOCOL

*Single Handed Carry*

Test Instructions:
Establish required linear walking distance. Container with tested reliability (including handle) should be used. Load the container with the required weight. Complete the full number of repetitions required from the start position to the end position of the required distance.using both hands to carry.

Complete the test pictured below as per the requirements listed on the front page. Follow the reps, load, frequency rate, and time requirements and any special instructions for completion of the task.

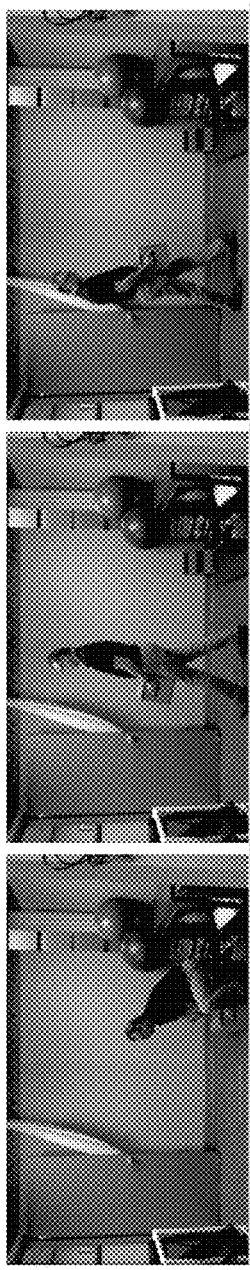

| Carrying | Force | Repetitions | Distance | Special Instructions |
|---|---|---|---|---|
| Single Handed Carry | 90 lbs | 1 rep | 20 feet | |

*Review and confirm the following for the test:*

The applicant was able to keep up with the timing required to complete the task.
The applicant was able to complete the repetitions required.
The applicant was able to maintain grip or grasp on the lifted object throughout testing and did NOT need to rest?
Excessive substitution patterns such as jerking, swaying, thrusting or shrugging were NOT observed.
Alternative body movements were NOT observed during the task (i.e swaying or rocking).
Excessive upper trap, cervical, or trunk muscular engagement were NOT used to complete task.
Excessive heavy breathing, profuse sweating, or flushing of the face were not present at the end of the test.
Applicant had no complaints of discomfort or pain during or after test.
Fatigue symptoms were NOT observed.

Notes:

FIG. 8D

Circuit Title: Mechanic Circuit

| Task No. | Circuit Activity Sequence | Mins per Activity | Duration/Distance | Reps to Complete | Load | Specific Instructions |
|---|---|---|---|---|---|---|
| 1 | Squat incline - pulley change out | 2 | 1 minute | Minimum 2 reps | No Load | Hold posture for 1 minute |
| 2 | Lift & Carry | 3 | 10 feet | Minimum 3 reps | 35 lbs | Lift and carry load 3 bouts of 10 feet |
| 3 | Kneeling | 3 | 15 Seconds | Minimum 10 reps | No Load | Hold posture for 1 minute |
| 4 | Single hand lift & carry | 3 | 10 feet | Minimum 4 reps | 30 lbs | Lift and carry load 3 bouts of 10 feet |
| 5 | Crouch balance - install/uninstall | 4 | 15 Seconds | Minimum 6 reps | 10 lbs | Hold posture for 2 minutes |
| 6 | Push test - install/unistalls | 0.5 | 30 Seconds | Minimum 2 reps | 45 lbs | Complete 2 reps of 45 lbs |
| 7 | Grip testing | 1 | NA | 5 Reps Position 3 | 20 lbs | Complete 5 reps of 20 lbs |
| 8 | Step/Climb | 0.5 | 30 Seconds | NA | No Load | Climb up and down for 30 seconds |
| 9 | Standing forward bend | 2 | 30 Seconds | Minimum 2 reps | 2 lbs | hold posture for 30 seconds twice |
| 10 | Side lying reach loaded | 2 | 15 Seconds | Minimum 2 reps | 5 lbs | hold posture for 15 seconds twice |
| 11 | Standing forward bend | 2 | 30 Seconds | Minimum 2 reps | 2 lbs | hold posture for 30 seconds twice |
| 12 | Reaching above shoulders loaded | 1 | 5 seconds | Minimum 2 reps | 2 lbs | Alternate arms holding 5 seconds at top |

Example task rotations

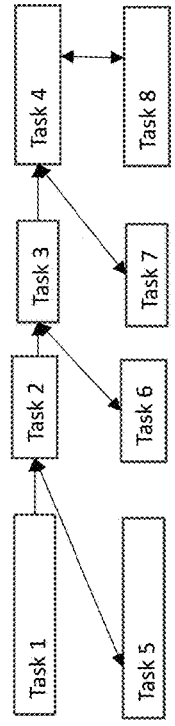

FIG. 9

| Item | Link | Photo |
|---|---|---|
| Knee pads | http://www.kneepro.com/ | |
| Gel Edge Protector | http://www.alimed.com/aliedge-gel-edge-protector.html | |
| Gel elbow pads | http://www.alimed.com/ulnar-gel-pads-gel-sleeves.html | |

FIG. 10A

**Company Name - Ergonomic Opportunities List - *Process Name***

| Priority Ranking | Observation | Opportunity | Recommendation |
|---|---|---|---|
|  | 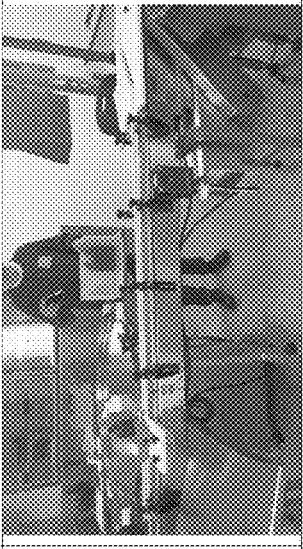 | Repetitive lifting and increased handling time. | Consider lowering the stand for the tote for the top of the tote is the same height as the conveyor. This will reduce the lifting height by 8 inches or more and should result in less handling time. |
|  |  | Potential for a serious cut | Consider utilizing cut resistant gloves and enforcing cut resistant glove policies. |
|  | 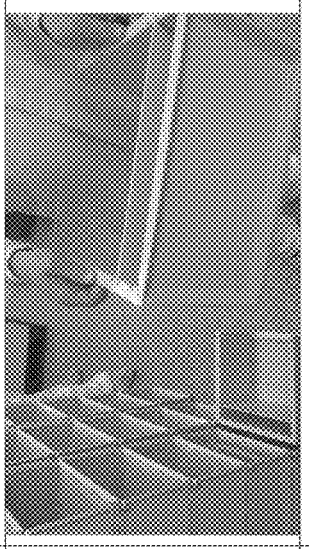 | Poor coupling between hand and totes | Consider phasing the current totes out to totes with good coupling. Contact me when investigating new totes and I can help determine specifications of hand holds. |

FIG. 10B

**Company Name – Ergonomic Opportunities List – *Process Name***

| | | |
|---|---|---|
| | Repetitive lifting and carrying | Investigate opportunities to decrease material handling and carrying distances. |
| | Repetitive awkward reaching postures associated with cleaning. | Work with quality and investigate opportunities to improve posture and duration.<br><br>- Ergonomic Team<br>- Engineering/Quality |
| | Repetitive awkward reaching postures associated with cleaning. | Work with quality and investigate opportunities to improve posture and duration.<br><br>- Ergonomic Team<br>- Engineering/Quality |
| | | |

FIG. 10C

**Company Name - Ergonomic Opportunities List - *Process Name***

| | | |
|---|---|---|
| | Repetitive awkward reaching postures associated with cleaning. | Work with quality and investigate opportunities to improve posture and duration.<br><br>- Ergonomic Team<br>- Engineering/Quality |
| 1 | The employee has to hold drum of powder in place and guide it as it falls. This task places the shoulder and elbow at significant risk of injury. | Consider utilizing drum chute.<br><br>- Ergonomic Team<br>- Engineering |

FIG. 11C

Posture and Positions

| Physical Demand | Task Numbers | Description of Task | DOT Level | Frequency of Physical Demand | Duration of Effort | Duration Without Recovery | Load or Force |
|---|---|---|---|---|---|---|---|
| STANDING | 2,3 | Standing | Occasional | 60/day | 2 minute | 30 minute | 0 Pounds |
| SITTING | 1 | Driving | Constant | 1/day | 12 hour | 12 hour | 0 Pounds |
| SQUATING | 3 | Blocking wheels | Occasional | 2/day | 5 second | 5 second | 10 Pounds |
| FORWARD BENDING(Active) | 3 | Checking wheels and breaks | Occasional | 1/day | 10 second | 10 second | 0 Pounds |
| KNEELING | 3 | Checking landing gear | Occasional | 1/day | 15 second | 15 second | 0 Pounds |
| SQUATING | 3 | Checking landing gear | Occasional | 1/day | 15 second | 15 second | 0 Pounds |
| FORWARD BENDING(Active) | 3 | Checking under trailer | Occasional | 20/day | 10 second | 3 minute | 0 Pounds |
| FORWARD BENDING(Sustained) | 3 | Checking landing gear | Occasional | 1/day | 20 second | 20 second | 0 Pounds |
| FORWARD BENDING(Active) | 3 | Checking lug nuts | Occasional | 10/day | 10 second | 3 minute | 0 Pounds |
| FOOT PRESS | 1 | Operating gas and break | Constant | 1/day | 12 hour | 12 hour | 20 Pounds |
| BALANCING | 2,3 | Balancing on elevated surfaces | Occasional | 8/day | 3 minute | 3 minute | 0 Pounds |
| SQUATING | 3 | squatting to adjust tandem | Occasional | 2/day | 15 second | 15 second | 0 Pounds |
| SQUATTING | | | Never | 0 | 0 | 0 | Never |
| OPERATING FOOT/LEG CONTROLS | | | Never | 0 | 0 | 0 | Never |
| SIDE BENDING | | | Never | 0 | 0 | 0 | Never |
| BACKWARD BENDING | | | Never | 0 | 0 | 0 | Never |
| TWISTING | | | Never | 0 | 0 | 0 | Never |

Copyright © 2017 by Ergonomics International, LLC

| Physical Demand | Task Numbers | Description of Task | DOT Level | Frequency of Physical Demand | Duration of Effort | Duration Without Recovery | Load or Force |
|---|---|---|---|---|---|---|---|
| LYING ON BACK | | | Never | 0 | 0 | 0 | Never |
| LYING ON SIDE | | | Never | 0 | 0 | 0 | Never |
| LYING ON STOMACH | | | Never | 0 | 0 | 0 | Never |
| LOOKING UPWARD | | | Never | 0 | 0 | 0 | Never |
| LOOKING DOWNWARD | | | Never | 0 | 0 | 0 | Never |
| DOT CLASSIFICATION | | Never (0% of workday) Frequent 34% - 66% of day | | | | Occasional 1% - 33% of day Constant 67% - 100% of day | |

Copyright © 2017 by Ergonomics International, LLC

FIG. 11E

Lifting

| Task Reference | Task Numbers | Description of Task | Start Height | End Height | Horizontal Distance | DOT Level | Frequency of Physical Demand | Duration of Effort | Duration Without Recovery | Load or Force | Coupling | Lifting Hands |
|---|---|---|---|---|---|---|---|---|---|---|---|---|
| L1 | | | 0 | 0 | 0 | Never | 0 | 0 | 0 | 0 | Never | Never |
| DOT CLASSIFICATION | | Never (0% of workday) Frequent 34% - 66% of day | | | | | Occasional 1% - 33% of day Constant 67% - 100% of day | | | | | |

Copyright © 2017 by Ergonomics International, LLC

FIG. 11F

Reaching

| Task Reference | Task Numbers | Description of Activity | Horizontal Distance | Vertical Distance | Forward | Side | Across Body | Behind | Above 57 inches | DOT Level | Frequency of Task | Duration of Effort | Duration Without Recovery | Load or Force | Right Hand, Left Hand, Both Hands, Either Hand, (R,L,B,E) |
|---|---|---|---|---|---|---|---|---|---|---|---|---|---|---|---|
| R1 | 3 | Inspecting tires | 20 inches | 45 inches | True | True | True | False | False | Occasional | 10/day | 5 second | 1 hour | 0 Pounds | Either Hand |
| R2 | 3 | Checking air filter and housing | 20 inches | 60 inches | True | True | True | False | True | Occasional | 1/day | 10 second | 10 second | 10 Pounds | Either Hand |
| R3 | 3 | Cables | 20 inches | 50 inches | True | True | True | False | False | Occasional | 4/day | 10 second | 10 second | 0 Pounds | Both Hands |
| R4 | 3 | Reaching to adjust tandem | 30 inches | 45 inches | False | True | False | False | False | Occasional | 2/day | 15 second | 15 second | 0 Pounds | Either Hand |
| R5 | 5 | Reaching to close and open doors | 20 inches | 60 inches | True | False | False | False | True | Occasional | 4/day | 5 second | 5 second | 0 Pounds | Both Hands |

Copyright © 2017 by Ergonomics International, LLC

FIG. 11G

Handling and Manipulation

| Physical Demand | Task Numbers | Description of Activity | DOT Level | Frequency of Task | Duration of Effort | Duration Without Recovery | Load or Force | Right Hand, Left Hand, Both Hands, Either Hand (R,L,B,E) |
|---|---|---|---|---|---|---|---|---|
| HAND GRASP | 3 | Checking tires | Occasional | 1/day | 5 minute | 1 hour | 15 Pounds | Either Hand |
| HAND GRASP | 3 | Inspection draining wet tank | Occasional | 1/day | 10 second | 10 second | 10 Pounds | Either Hand |
| HAND GRASP | 1,3 | Fuel cap | Occasional | 2/day | 5 second | 5 second | 10 Pounds | Either Hand |
| LATERAL PINCH (THUMB & LATERAL FINGER) | 3 | Checking oil | Occasional | 1/day | 10 second | 10 second | 0 Pounds | Either Hand |
| FINGER MANIPULATION | 1 | Operating controls | Occasional | 6/hour | 2 second | 2 second | 1 Pounds | Right Hand |
| TWO FINGER PULL | 3 | Checking oil | Occasional | 1/day | 10 second | 10 second | 5 Pounds | Both Hands |
| WRITING | 1,3 | Writing | Occasional | 2/day | 1 minute | 1 minute | 0 Pounds | Either Hand |
| HAND GRASP | 1 | Grasping steering wheel | Constant | 1/day | 12 hour | 12 hour | 15 Pounds | Both Hands |
| HAND GRASP | 3 | Cables | Occasional | 4/day | 10 second | 10 second | 20 Pounds | Both Hands |
| HAND GRASP | 2,2 | Lowering and raising landing gear | Occasional | 2/day | 20 second | 20 second | 50 Pounds | Both Hands |
| HAND PRESS | 5 | Closing doors | Occasional | 4/day | 5 second | 5 second | 50 Pounds | Both Hands |
| HOLDING | | | Never | 0 | 0 | 0 | 0 | Never |
| HOOK GRASP | | | Never | 0 | 0 | 0 | 0 | Never |
| CHUCK PINCH (THUMB & 2 FINGERS) | | | Never | 0 | 0 | 0 | 0 | Never |

Copyright © 2017 by Ergonomics International, LLC

FIG. 11H

| Physical Demand | Task Numbers | Description of Activity | DOT Level of Activity | Frequency of Task | Duration of Effort | Duration Without Recovery | Load or Force | Right Hand, Left Hand, Both Hands, Either Hand, (R,L,B,E) |
|---|---|---|---|---|---|---|---|---|
| PULP PINCH (THUMB & TIP OF FINGER) | | | Never | 0 | 0 | 0 | 0 | Never |
| THUMB OR FINGER PRESS | | | Never | 0 | 0 | 0 | 0 | Never |
| KEYING/10 KEY OPERATION | | | Never | 0 | 0 | 0 | 0 | Never |
| POWER TOOLS | | | Never | 0 | 0 | 0 | 0 | Never |
| PNEUMATIC TOOLS | | | Never | 0 | 0 | 0 | 0 | Never |
| HAND TOOLS | | | Never | 0 | 0 | 0 | 0 | Never |
| CUTTING WITH KNIFE | | | Never | 0 | 0 | 0 | 0 | Never |
| CUTTING WITH SCISSORS OR SHEARS | | | Never | 0 | 0 | 0 | 0 | Never |
| DOT CLASSIFICATION | | Never (0% of day) Frequent (34-66% of day) | | | | Occasional (0%-33% of day) Constant (67%-100% of day) | | |

Copyright © 2017 by Ergonomics International, LLC

FIG. 11I

Transporting

| Physical Demand | Task Numbers | Description of Task | DOT Level | Frequency of Task | Duration of Effort | Duration Without Recovery | Load or Force | Distance |
|---|---|---|---|---|---|---|---|---|
| WALKING | 2, 3, 5 | Walking around truck | Occasional | 12/day | 3 minute | 30 minute | 0 Pounds | 200 Feet |
| CLIMBING STEPS/STAIRS | 1 | Climbing in and out of equipment | Occasional | 8/day | 3 second | 3 second | 0 Pounds | 4 Feet |
| PUSHING (DYNAMIC) | 3 | Opening hood during inspection | Occasional | 1/day | 5 second | 5 second | 45 Pounds | 4 Feet |
| CRAWLING | 3 | Inspection | Occasional | 1/day | 15 second | 15 second | 0 Pounds | 3 Feet |
| CLIMBING STEPS/STAIRS | 2, 3 | Climbing on trailer | Occasional | 2/day | 3 second | 3 second | 0 Pounds | 14 Inches |
| PULLING (STATIC) | 2, 3 | Releasing king pin | Occasional | 1/day | 5 second | 5 second | 50 Pounds | 0 Inches |
| PULLING (DYNAMIC) | 2, 3 | Raising or lowering landing gear | Occasional | 2/day | 20 second | 20 second | 50 Pounds | 24 Inches |
| PUSHING (DYNAMIC) | 2, 3 | Lowering or raising landing gear | Occasional | 2/day | 20 second | 20 second | 50 Pounds | 24 Inches |
| DUAL ARM CRANKING | 2 | Lowering or raising dolly legs | Occasional | 2/day | 5 minute | 5 minute | 20 Pounds | 12 Inches |
| PUSHING (STATIC) | 2 | Closing trailer doors | Occasional | 4/day | 5 second | 5 second | 50 Pounds | 0 Inches |
| PUSHING (DYNAMIC) | 5 | Pushing pallet jack | Frequent | 80/day | 3 minute | 3 hour | 30 Pounds | 50 Yards |
| PULLING (DYNAMIC) | 5 | Pulling pallet jack | Occasional | 40/day | 3 minute | 3 hour | 30 Pounds | 50 Yards |
| PULLING (STATIC) | 3 | Pulling to adjust tandem | Occasional | 2/day | 5 second | 5 second | 30 Pounds | 0 Feet |
| WALKING BACKWARDS | | | Never | 0 | 0 | 0 | 0 | 0 |
| CARRYING (BOTH HANDS) | | | Never | 0 | 0 | 0 | 0 | 0 |

Copyright © 2017 by Ergonomics International, LLC

FIG. 11J

| Physical Demand | Task Numbers | Description of Task | DOT Level | Frequency of Task | Duration of Effort | Duration Without Recovery | Load or Force | Distance |
|---|---|---|---|---|---|---|---|---|
| CARRYING (SINGLE HAND) | | | Never | 0 | 0 | 0 | 0 | 0 |
| CARRYING (SINGLE OR DOUBLE STRAP LOAD) | | | Never | 0 | 0 | 0 | 0 | 0 |
| SINGLE ARM CRANKING | | | Never | 0 | 0 | 0 | 0 | 0 |
| CLIMBING LADDER | | | Never | 0 | 0 | 0 | 0 | 0 |
| TOSSING (WRIST/HAND) | | | Never | 0 | 0 | 0 | 0 | 0 |
| THROWING (SHOULDER) | | | Never | 0 | 0 | 0 | 0 | 0 |
| SWEEPING/MOPPING | | | Never | 0 | 0 | 0 | 0 | 0 |
| SHOVELING | | | Never | 0 | 0 | 0 | 0 | 0 |
| RIDING BICYCLE | | | Never | 0 | 0 | 0 | 0 | 0 |
| RIDING MOTORCYCLE | | | Never | 0 | 0 | 0 | 0 | 0 |
| RIDING TRICYCLE | | | Never | 0 | 0 | 0 | 0 | 0 |
| DIGGING | | | Never | 0 | 0 | 0 | 0 | 0 |
| STRIKING (HAMMER/PICK/AXE) | | | Never | 0 | 0 | 0 | 0 | 0 |
| DRIVING SMALL VEHICLE | | | Never | 0 | 0 | 0 | 0 | 0 |
| DRIVING LARGE VEHICLE | | | Never | 0 | 0 | 0 | 0 | 0 |
| DOT CLASSIFICATION | Never (0% of workday) Frequently (34% - 65% of day) | | | | | Occasional (1% - 33% of day) Continual (66% - 100% of day) | | |

Copyright © 2017 by Ergonomics International, LLC

FIG. 11K

Environmental Conditions

| Physical Demand | Task Numbers | Description of Task | DOT Level | Frequency of Task | Duration of Event | Duration Without Recovery |
|---|---|---|---|---|---|---|
| WORKING OUTDOORS IN WEATHER | 2 | Working outside to secure load | Occasional | 1/day | 30 minute | 30 minute |
| WORKING OUTDOORS IN WEATHER | 3 | Working outside when inspecting truck | Occasional | 1/day | 1 hour | 1 hour |
| WORKING IN SPECIAL CLOTHING | 2, 3, 5 | Standard PPE for each task | Occasional | 2/day | 1 hour | 1 hour |
| WORKING AT HEIGHTS | | | Never | 0 | 0 | 0 |
| WORKING IN NOISE ABOVE 80dB | | | Never | 0 | 0 | 0 |
| WORKING WITH VIBRATION (HAND ARM) | | | Never | 0 | 0 | 0 |
| WORKING WITH VIBRATION (WHOLE BODY) | | | Never | 0 | 0 | 0 |
| WORKING IN WET ENVIRONMENT | | | Never | 0 | 0 | 0 |
| WORKING IN HIGH HEAT | | | Never | 0 | 0 | 0 |
| WORKING IN COLD ENVIRONMENT | | | Never | 0 | 0 | 0 |
| WORKING IN DUST ENVIRONMENT | | | Never | 0 | 0 | 0 |
| WORKING IN CONFINED SPACE | | | Never | 0 | 0 | 0 |
| WORKING WITH RADIATION | | | Never | 0 | 0 | 0 |
| WORKING WITH TOXIC OR CAUSTICS | | | Never | 0 | 0 | 0 |
| WORKING WITH EXPLOSIVES OR FIRE | | | Never | 0 | 0 | 0 |
| WORKING WITH ELECTRICITY | | | Never | 0 | 0 | 0 |
| WORKING IN ATMOSPHERIC CONDITIONS | | | Never | 0 | 0 | 0 |
| WORKING AROUND MOVING PARTS | | | Never | 0 | 0 | 0 |
| Physical Demand | Task Numbers | Description of Task | DOT Level | Frequency of Task | Duration of Event | Duration Without Recovery |
| DOT CLASSIFICATION | | Never 0% of work day Frequent 33% cost of day | | | Occasional 1% - 33% of day Constant 67% - 100% of day | |

10-11

Copyright © 2017 by Ergonomics International, LLC

FIG. 11L

Sensations

| Physical Demand | Task Numbers | Description of Task | DOT Level | Frequency of Task | Duration of Event | Duration Without Recovery |
|---|---|---|---|---|---|---|
| JOB TASK REQUIRES SMELL | | | Never | 0 | 0 | 0 |
| JOB TASK REQUIRES TASTE | | | Never | 0 | 0 | 0 |
| JOB TASK REQUIRES HEARING | | | Never | 0 | 0 | 0 |
| JOB REQUIRES SPECIFIC VISION LEVELS | | | Never | 0 | 0 | 0 |
| JOB REQUIRES SPECIFIC TACTILE ABILITY | | | Never | 0 | 0 | 0 |
| JOB REQUIRES ABILITY TO SEE COLOUR | | | Never | 0 | 0 | 0 |
| TEMPERATURE DISCRIMINATION | | | Never | 0 | 0 | 0 |
| DEPTH PERCEPTION | | | Never | 0 | 0 | 0 |
| DOT CLASSIFICATION | | | Never 0% of work day | | | Occasional 1% - 33% of day |
| | | | Frequent 34% - 66% of day | | | Constant 67% - 100% of day |

Copyright © 2017 by Ergonomics International, LLC

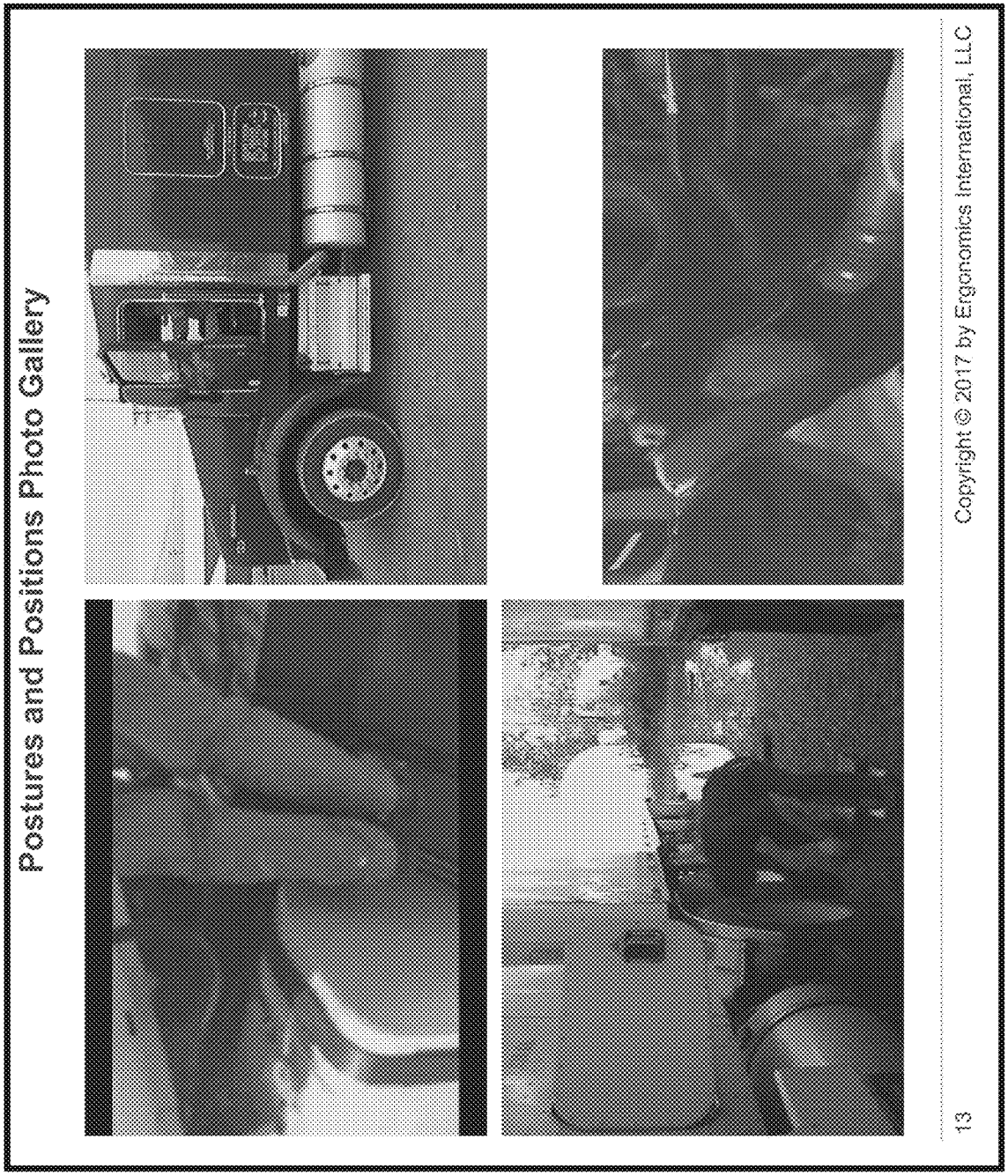

WORKSITE RISK ANALYSIS AND DOCUMENTATION SYSTEM AND METHOD

CROSS-REFERENCE TO RELATED APPLICATIONS

The present application claims priority to U.S. Provisional Application Ser. No. 62/446,843 filed on Jan. 17, 2017 entitled "A Video Based Visual Worksite Analysis Documentation System", the disclosure of which is hereby incorporated in its entirety at least by reference.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention generally relates to health and safety, and more particularly to a worksite risk analysis and documentation system and method.

2. Description of Related Art

Health and safety are primary concerns for companies relating to worksite tasks performed by company employees. Further, the majority of worksite injuries are associated with exposure to ergonomic risk factors. Thus, calculating risks and opportunities relating to specific job tasks are critical, and documenting the system is paramount. There is a strong need for standardization of terminology and calculated methods for physical demands. Companies need a stronger way to identify physical capabilities of new hires, incumbents, and return to work candidates. Consequently, there is a need for a worksite risk analysis and documentation system and method.

BRIEF SUMMARY OF THE INVENTION

In one embodiment of the present invention a system is provided, the system comprising an Internet-connected computerized appliance having a processor and coupled to a data repository, the processor executing software from a non-transitory storage medium, the software providing an interactive interface to a worksite risk analysis and documentation system, the system enabling a user to: log on; upload video data from a camera or a mobile device; capture a plurality of images from the video data to document physical demands and ergonomic risk/opportunities corresponding to a plurality of tasks at a worksite; analyze each image of the plurality of images to each task of the plurality of tasks as either a physical demand or an ergonomic risk/opportunity; assign each image of plurality of images as either essential or non-essential functions of each task; utilize a database of definitions to define and standardize the essential and non-essential functions of each task; calculate DOT classification levels to produce a category of work level corresponding to each task for each image categorized as physical demands, wherein the category of work level includes at least one of sedentary work, light work, medium work, heavy work, and very heavy work; store the plurality of images in the non-transitory storage medium; and generate a final report, wherein the final report includes the plurality of images, the plurality of tasks, the calculated DOT classifications levels, and physical demand descriptions.

In one embodiment, the system further enabling the user to: create an ergonomic risk/opportunity list, wherein the ergonomic risk opportunity list includes a priority ranking for each observation corresponding to each image of the plurality of images to each task of the plurality of tasks analyzed as an ergonomic risk/opportunity, a description of the ergonomic opportunity/risk, and a recommendation to improve the ergonomic opportunity risk. In another embodiment, the system further enabling the user to: identity specific body parts affected by the physical demands. In one embodiment, the system further enabling the user to: create a body part based risk report for each task of the plurality of tasks including at least one body part, wherein each body part of the at least one body part having an individual injury cost, such that the system is configured to prioritize a risk value for each body part of the at least one body part. In yet another embodiment, the system further enabling the user to: create a report, wherein the report includes a solution catalog of engineered solutions and administrative control solutions for the body part based risk report.

In another aspect of the invention, a method is provided, comprising steps (a) providing training and credentialing of a plurality of users for use of a worksite risk analysis and documentation system; (b) recording video data via a camera or a mobile device at a worksite; (c) enabling a user of the plurality of users to access the worksite risk analysis and documentation system from a geographical location via an Internet connection; (d) enabling the user to upload the video; (e) capturing a plurality of images from the video data to document physical demands and ergonomic risk/opportunities corresponding to a plurality of tasks at the worksite; (f) analyzing each image of the plurality of images to each task of the plurality of tasks as either a physical demand or an ergonomic risk/opportunity: (g) assigning each image of plurality of images as either essential or non-essential functions of each task; (h) accessing a database of definitions to define and standardize the essential and non-essential functions of each task; (i) calculating DOT classification levels to produce a category of work level corresponding to each task for each image categorized as physical demands, wherein the category of work level includes at least one of sedentary work, light work, medium work, heavy work, and very heavy work; (j) storing the plurality of images in the non-transitory storage medium; and (k) generating a final report, wherein the final report includes the plurality of images, the plurality of tasks, the calculated DOT classifications levels, and physical demand descriptions.

In one embodiment, a further step is provided of creating an ergonomic risk/opportunity list, wherein the ergonomic risk opportunity list includes a priority ranking for each observation corresponding to each image of the plurality of images to each task of the plurality of tasks analyzed as an ergonomic risk/opportunity, a description of the ergonomic opportunity/risk, and a recommendation to improve the ergonomic opportunity risk. In another embodiment, a further step is provided of identifying specific body parts affected by the physical demands. In one embodiment, a further step is provided of creating a body part based risk report for each task of the plurality of tasks including at least one body part, wherein each body part of the at least one body part having an individual injury cost, such that the system is configured to prioritize a risk value for each body part of the at least one body part. In yet another embodiment, a further step is provided of creating a report, wherein the report includes a solution catalog of engineered solutions and administrative control solutions for the body part based risk report.

BRIEF DESCRIPTION OF THE SEVERAL VIEWS OF THE DRAWINGS

Other features and advantages of the present invention will become apparent when the following detailed description is read in conjunction with the accompanying drawings, in which:

FIG. 4 shows an exemplary data collected from a worker interview of FIG. 3.

FIG. 5 shows an exemplary data collected from job review, including interview and observational evaluations of FIG. 3.

FIG. 6 shows an exemplary body part risk report of FIG. 3.

FIGS. 8A-C show a number of exemplary testing reports according to an embodiment of the present invention.

FIG. 8D shows an exemplary circuit for a testing protocol according to an embodiment of the present invention.

FIG. 9 shows an exemplary engineered solution page of FIG. 7.

FIGS. 10A-C show an exemplary ergonomic risk/opportunities report according to an embodiment of the present invention.

DETAILED DESCRIPTION OF THE PREFERRED EMBODIMENT

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a worksite risk analysis and documentation system and method.

The word "a" is defined to mean "at least one." The terminology includes the words above specifically mentioned, derivatives thereof, and words of similar import. "Worksite" and "workplace" may be used interchangeably herein, and is defined as a place (such as a shop, factory, office, or area of land) where work is done, performed, completed, built, or assembled by workers.

In one embodiment, the worksite risk analysis and documentation system and method defines, captures, categorizing, documents, while analyzing functional physical demands of a plurality of jobs at various worksites, including environmental health and safety risks/opportunities as well as ergonomic risks/opportunities.

Figure 1A:
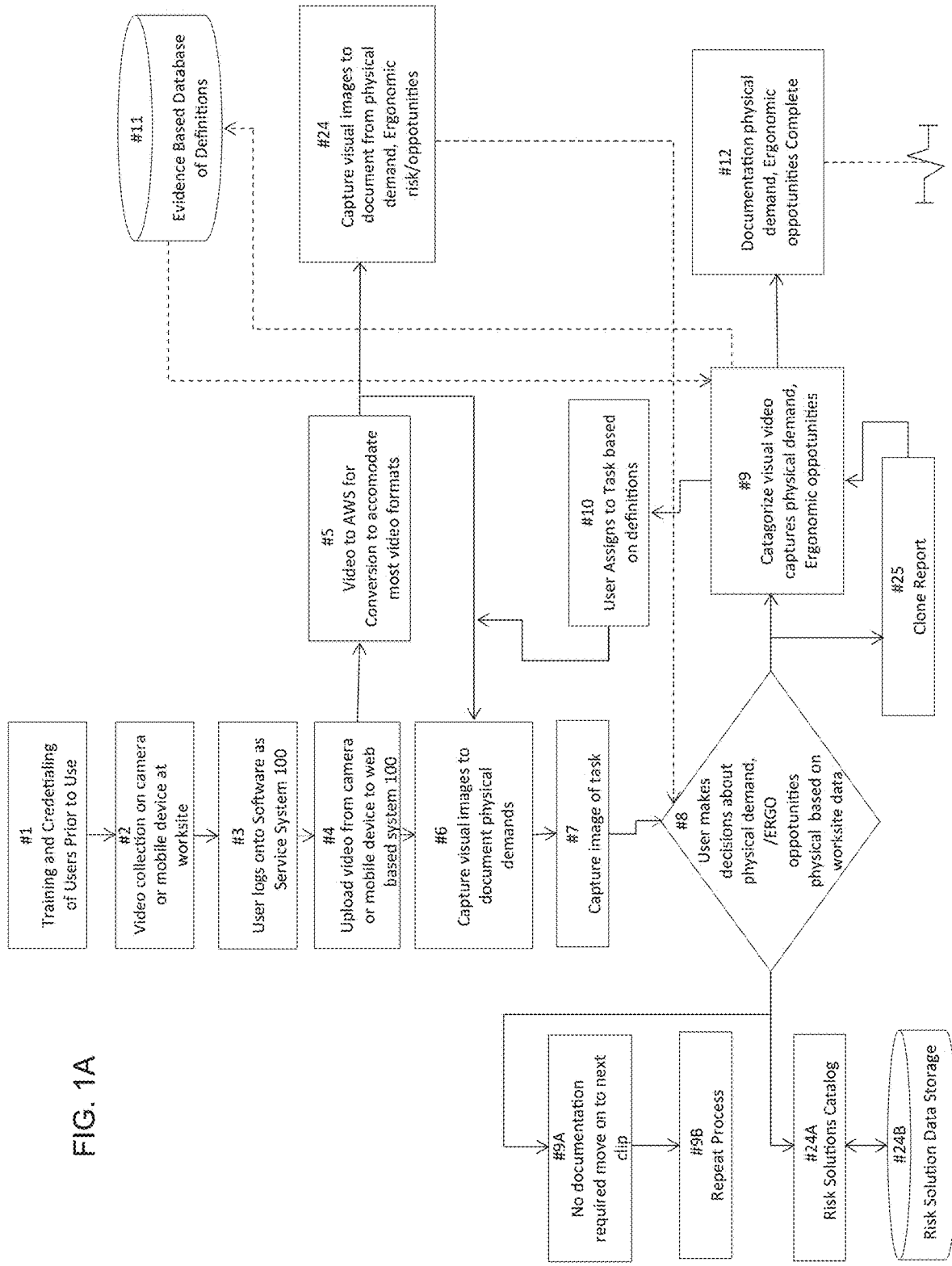
FIGS. 1A-C is a flow diagram for a worksite risk analysis and documentation system and method according to an embodiment of the present invention.
Figure 1B:
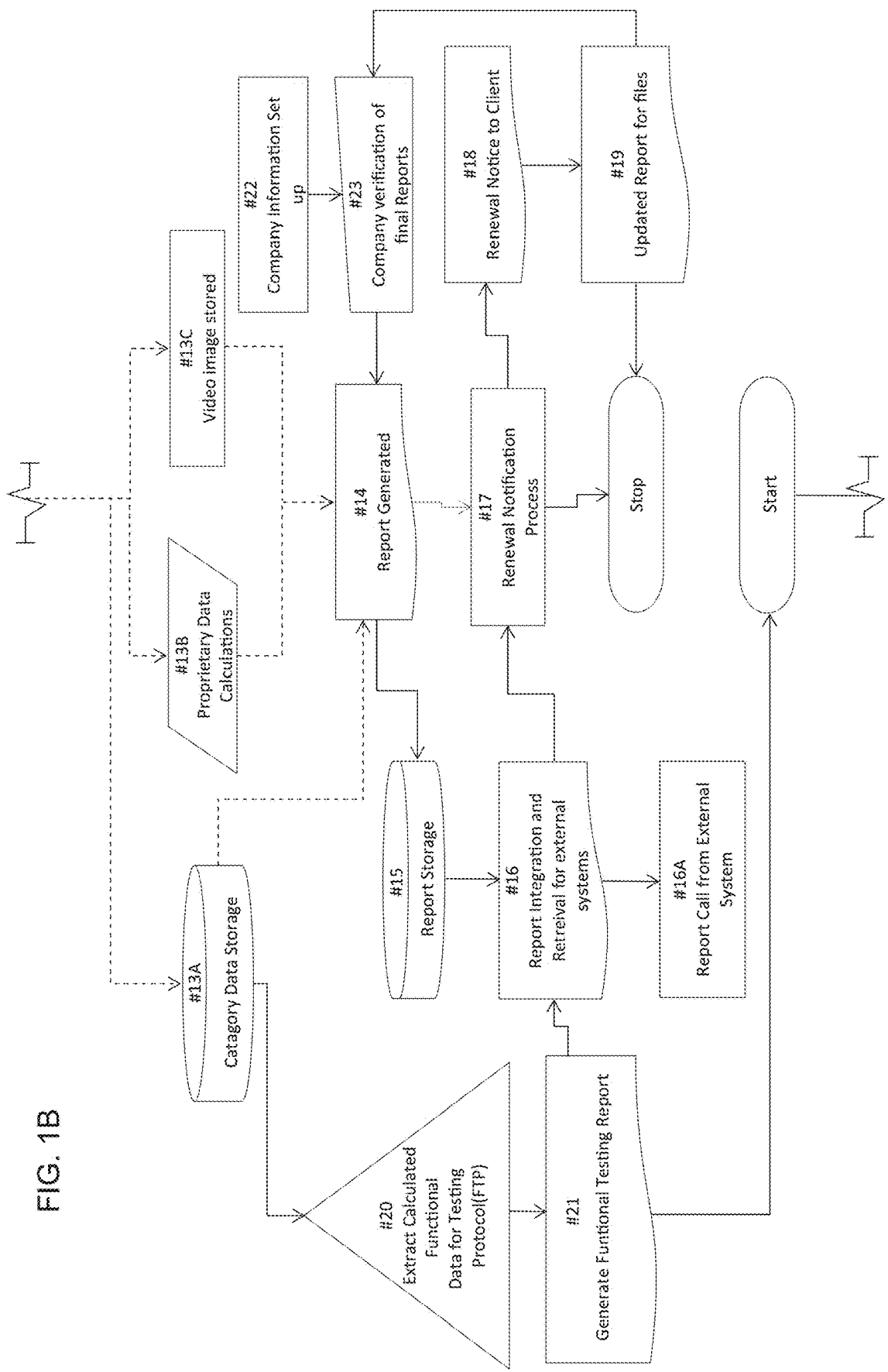
Figure 1C:
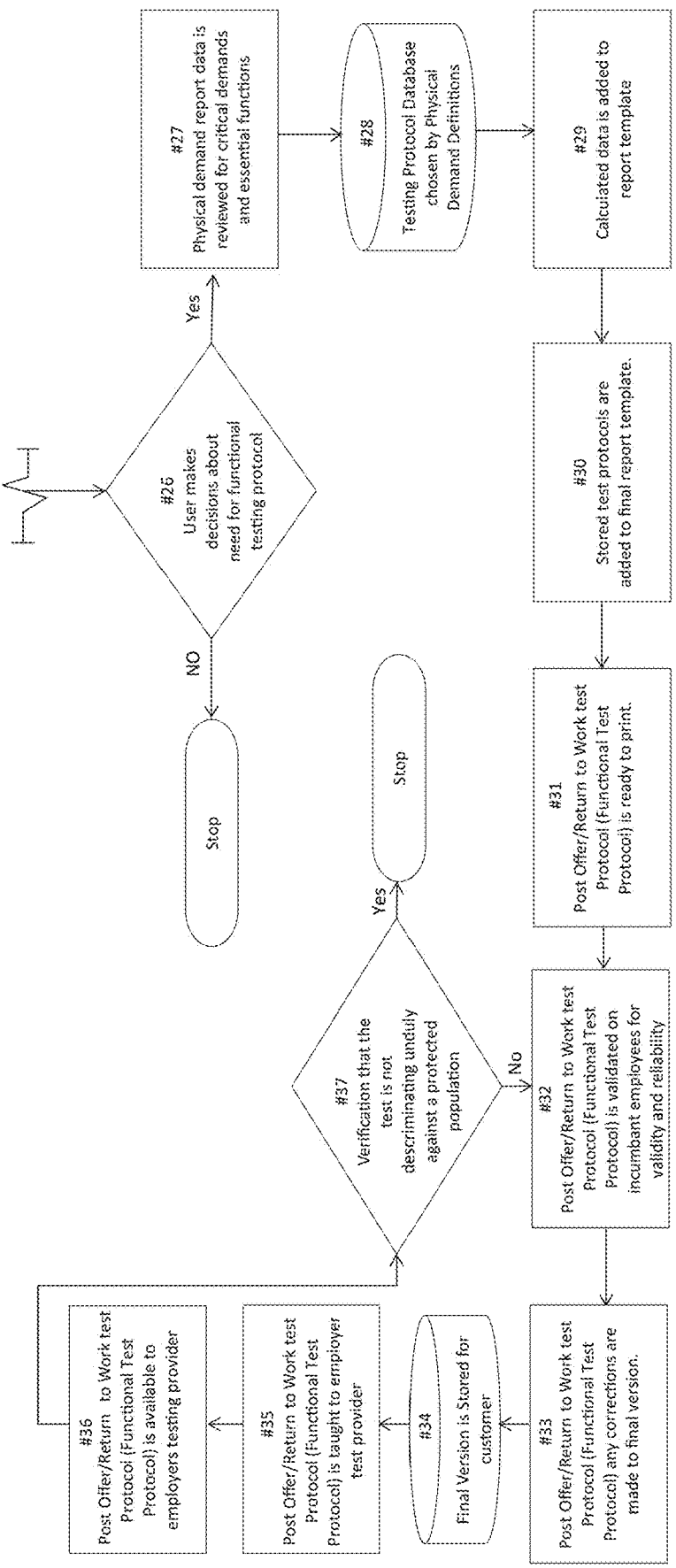

In one embodiment, the worksite risk analysis and documentation system allows a user to perform the following tasks: define functional physical demands associated with specific job tasks using evidence based definitions, upload video data from camera or mobile devices, visually display and capture worksite images from video data, visually document task based essential functions and physical demands for the development of task specific functional testing protocols, visually document EHS risks and opportunities through visual and pdf export, determine Dictionary of Occupational Title Work Levels by proprietary calculations, manage multiple physical demands of the same type e.g. multiple reaches or lifts, calculate Dictionary of Occupational Title work defined levels, calculate Ergonomic Risk Components by Job Task, calculate EHS Risk Components by Job Task, integrate the system with Functional Capacity Assessment Software System, provide evidenced based definitions of physical demands of work, produce image based reports, provide report revision protection, clone reports and store for future uses and integrations, store images for reporting, and access assess the system on the Internet FIGS. 1A-C is a flow diagram for a worksite risk analysis and documentation system and method according to an embodiment of the present invention. Referring to now to FIGS. 1A-C, the method of using the worksite risk analysis and documentation system is provided. In step 1, the training and credentialing of users for use of the system is provided. This is critical to maintaining and standardizing the method steps or process of the worksite risk analysis and documentation system. The training environment can vary, for instance, in one embodiment training is in a class room setting, typically over two full days, wherein the users are provided learning materials of the system. In another embodiment, the training is completed online and on demand at the user's pace. Credentialing is required to insure users are qualified to perform various tasks, including but not limited to assessments which are annually renewed. In one embodiment, a user's credential is annually renewed to prove capabilities and knowledge of the system to maintain credential status. In one embodiment, a user's credential status is subject to an annual review of reports the user completed over the previous year. In one embodiment, the training and credentialing is assessed with various testing methods as well known in the art. Step 1 is critical, as without specific and explicit training in the details of the system and method, the system loses validity and reliability.

In step 2, video data is recorded via a camera or a mobile device at a worksite. The video data provides the foundation of worksite risk analysis and documentation system and method. In one embodiment, an evaluator records a video displaying at least one of a physical demand required by a worker, an ergonomic concern involving a worker, and an environmental health and safety concern involving a worker. In one embodiment, the video data can be recorded on any video camera or mobile device. The video data provides the opportunities which are evaluated, analyzed, and mitigated by the method described herein. This is a particular advantage of the present invention as it provides a consistent and standardized process for which employers can measure, collect, visually document, report, store, and recall data which has previously been done on paper or in spreadsheets in the systems found in the prior art.

In step 3, a user logs into the system 100. The system architecture will be explained in further detail below. The log-in portal of the system allows for a single point of entry into the system, which provides security measures for system. In one embodiment, the system logs entry of any user that accesses the system users, while establishing the location of data in the system based on specific user and company in which the user is affiliated. In another embodiment, the system allows for annual renewal tracking of users and allows for integration of report cloning features. In one embodiment, security measures are required when accessing the system, such as usernames, passwords, and other security tokens as well known in the art, only allowing trained and qualified user access to the system while preventing unauthorized access.

Figure 2:
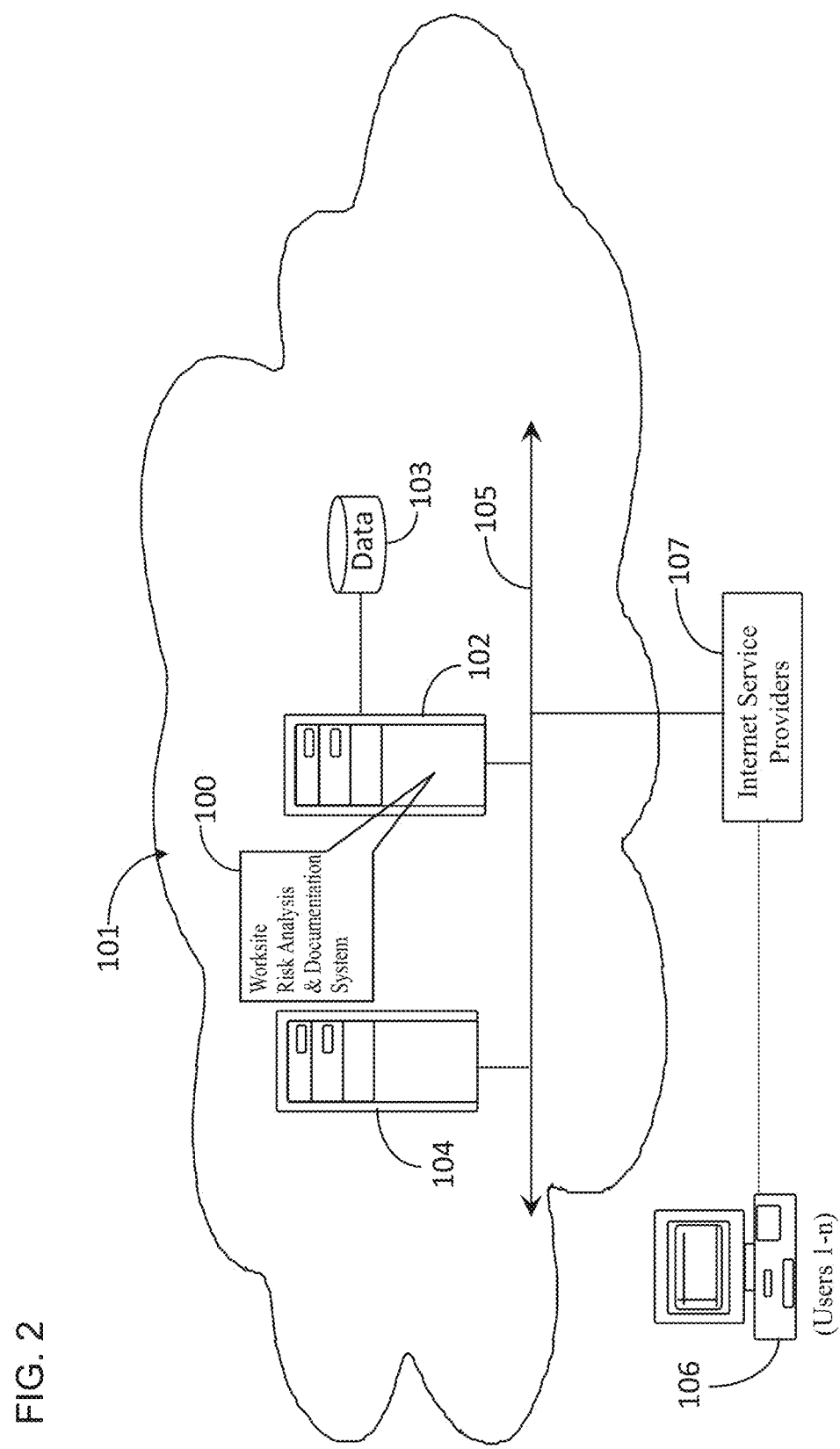
FIG. 2 is an architectural diagram of an Internet computer network system according to an embodiment of the present invention.

In step 4, the video data is uploaded to the system 100. This is the initial step required for all reporting, documentation, calculations, and analysis of the physical demands, ergonomic concerns, and environmental health and safety (EHS) concerns as previously described. In this step, the user can also isolate each demand, concern, risk, or opportunity into separation documentation files. In one embodiment, the system allows the user to view and manage video data on a single screen. In one embodiment, the system allows image capture that is linked to either an opportunity or physical demand. Further, the system allows for the use of a single image for multiple opportunities or physical demands without leaving the initial captured image. It is a particular advantage of the present invention, that the system allows the user to move through the video data on the screen capturing as many individual and uniquely identified images associated with the physical demands or opportunities noted in the workplace. It is important to note that the video data at this point of the process. This provides security to companies and users within the system in that actual video footage is only used for the capturing of images rather than storing complete video. Images are stored after user has defined and saves them to a data repository 103 on server 102 (FIG. 2).

In step 5, the video data may be converted from various camera formats, allowing end users flexibility in devices that can be used. This provides options for mobile users to collect on the fly and convert, insuring compatibility to current and future formats. This step is only performed if required. In one embodiment, a file converter is used for Apple devices, to convert from Apple formats to PC compatible file types if necessary as well known in the art. The object is to provide consistency and a standardized format.

In step 6 or 24 depending on the concern, the visual images to document and analyze physical demand, ergonomic risk/opportunities. Specifically, in step 6, ergonomic risk factors are used to create an ergonomic risk opportunity list (FIG. 10A-C). In one embodiment, the ergonomic risk opportunity list includes a priority ranking for each observation/visual image, a description of the opportunity/risk, and a recommendation to improve the opportunity risk. In step 24, ergonomic risk factors and opportunities and physical demand captured images are isolated via dropdown commands. These dropdowns identify specific body parts affected by physical demand, exposure, and the number of person affected by the risk. The system then calculates, using a programmed dollar amount (customer or data set), a prioritized risk matrix. In one embodiment, the prioritized risk matrix is then linked to a catalogue of solutions including administrative, engineered or personal protective equipment (PPE) which can aid in mitigating the problem. An embodiment of a prioritized risk matrix will be discussed in greater detail below.

In step 7, an image of the task is captured. Specifically, a user can isolate and link opportunities and physical demands using dropdown commands on the various screens of the system. These dropdowns identify specific physical demands, EHS opportunities, and ergonomic opportunities. Specifics of these identifiers are determined by the research, industry standards and defined definitions provided within the system. This process provides, data storage of single image opportunities in multiple categories from a single user screen and sets of dropdown menus of researched and defined details that will be associated with that image in a visual report. The visual report will be described in further detail below.

In step 8, the user makes a decision about EHS, ergonomic, physical demand, and/or risk/opportunity. At this step, the user also begins deciding what they want to collect from the captured image and how many categories it will apply to. Further, the user defines the type of visual report that will be produced as an outcome. The user identifies the critical initial data that needs to be collected and linked to a specific captured image. In one embodiment, the user identifies dropdown information that needs to be linked with the image. It should be understood that the training as described in step 1 is necessary to perform this step, as the definitions are required to be understood and it requires users to understand the differences between physical demand and ergonomic risk. Further, users are required to know EHS concerns and mitigation strategies.

In step 9, the user analyzes the images previously captured from the video date into physical demand, EHS or Ergonomic risk/opportunities. Specifically, the user decides what they want to collect from the captured image and how many categories it will apply to. In one embodiment, the user defines the type of visual report that will be produced as an outcome. The user identifies the critical initial data that needs to be collected and linked to a specific captured image. In one embodiment, the user also identifies dropdown information that needs to be linked with the image.

In step 10, the user assigns the previously categorized images in step 9 to a task. Specifically, the user divides the captured images into essential and non-essential functions of a job. In one embodiment, the user creates a process for accommodating physical or cognitive deficits for return to work, ADA (Americans with Disabilities Act) accommodation strategies, risk reduction, or safety issue mitigation. In one embodiment, the division between essential and non-essential functions of a job can be visually reported format for employers, physicians, safety managers, case managers, or legal personnel. The visual clarification of essential and non-essential functions allows for faster decisions on accommodations, mitigation, or prioritization.

In step 11, utilizing the evidence based database of definitions, objectifies, standardizes, and clarifies how the end user categorizes the linked data associated with captured images, resulting in continually improving system of defining the data being used for analysis and visual reports. This is a critical step of the system, as it standardizes the details by every user of the system as well as the standardization of definitions for end users of the visual reports. This is a particular advantage of the present invention, as it's the only system and process to have defined physical demands, environmental conditions, or sensory criteria based on peer reviewed literature. Further, it's the only system to actually calculate DOT levels incorporating work rest criteria as well as the only system to establish work levels based on uploaded video data.

In step 12, the user assigns the previously categorized images in step 9 to a task. Specifically, the user divides the captured images into essential and non-essential functions of a job. In one embodiment, the user creates a process for accommodating physical or cognitive deficits for return to work, ADA (Americans with Disabilities Act) accommodation strategies, risk reduction, or safety issue mitigation. In one embodiment, the division between essential and non-essential functions of a job can be visually reported format for employers, physicians, safety managers, case managers, or legal personnel. The visual clarification of essential and non-essential functions allows for faster decisions on accommodations, mitigation, or prioritization. After this step, the documentation process is complete.

In step 13A, the data storage is categorized. The Dictionary of Occupational Titles (DOT) calculations produce a category of work level. This level is then stored for the reporting process. Levels are calculated and confirmed to specified definitions within the system. It is a particular advantage of the present invention that the system uniquely calculates DOT levels based on mathematical criteria. The DOT levels for physical demand can be defined as sedentary work, light work, medium work, heavy work, and very heavy work.

In one embodiment, sedentary work is defined as exerting up to 10 pounds of force occasionally and/or a negligible amount of force to lift, carry, push, pull, or otherwise move objects, including the human body. Sedentary work involves sitting most of the time, but may involve walking or standing for brief periods of time. Jobs are sedentary if walking and standing are required only occasionally and all other sedentary criteria are met.

In one embodiment, light work is defined as exerting up to 20 pounds of force occasionally, and/or up to 10 pounds of force frequently, and/or a negligible amount of force constantly to move objects. Physical demand requirements are in excess of those for sedentary work. Even though the weight lifted may be only a negligible amount, a job should be rated Light Work: (a) when it requires walking or standing to a significant degree; or (b) when it requires sitting most of the time but entails pushing and/or pulling of arm or leg controls; and/or (c) when the job requires working at a production rate pace entailing the constant pushing and/or pulling of materials even though the weight of those materials is negligible. It is important to note that the constant stress and strain of maintaining a production rate pace, especially in an industrial setting, can be and is physically demanding of a worker even though the amount of force exerted is negligible.

In one embodiment, medium work is defined as exerting 20 to 50 pounds of force occasionally, and/or 10 to 25 pounds of force frequently, and/or greater than negligible up to 10 pounds of force constantly to move objects. Physical demand requirements are in excess of those for light work.

In one embodiment, heavy work is defined as exerting 50 to 100 pounds of force occasionally, and/or 25 to 50 pounds of force frequently, and/or 10 to 20 pounds of force constantly to move objects. Physical demand requirements are in excess of those for medium Work.

In one embodiment, very heavy work is defined as exerting in excess of 100 pounds of force occasionally, and/or in excess of 50 pounds of force frequently, and/or in excess of 20 pounds of force constantly to move objects. Physical demand requirements are in excess of those for heavy work.

The frequencies of the aforementioned DOT levels described above were previously described above by the terms occasionally (or occasional), frequently (or frequent), and constantly or (constant), which can be defined as activity or condition exists up to ⅓ of the time, ⅓ to ⅔ of the time, and more than ⅔ of the time respectively. For instance, assuming an 8 hour work day, there are 28,800 seconds in the day. The frequency of a physical demand multiplied by the duration can determine which type of DOT level is required for a specific job. That is, the DOT level and physical demands reflects the estimated overall strength requirement of the job, representing the strength requirements which are considered to be important for average, successful work performance. Thus, if the frequency of a physical demand multiplied by the duration is: greater than or equal to 1 second and less than or equal to 9,504 seconds the result is occasional, greater than or equal to 9,505 seconds and less than or equal to 19,008 seconds the result is frequent, and greater than or equal to 19,009 seconds the result is constant.

In step 13B, the data calculations of step 13A are performed for each occurrence of physical demand. These calculations objectify, standardize, and clarify how the end user establishes calculated findings regarding the final report. Further, data calculations reduce error and standardize user report findings. Proprietary data calculations are established by peer reviewed literature and definitions. Standardization of calculations occurs for every user in the same way, which reduces error in reporting, while improving the capability to stand up legal scrutiny.

In step 13C, the video image is stored. Specifically, the individually selected images are categorized and tagged with specific components for reporting process, allowing the user to edit, clone, or revise the selections. Then, the images are embedded into final report formatting and attached to specific details in the final report.

In step 14, the final report is generated. The final report is a visually documented report including images, calculated results, recommendations, accommodations, tasks, locations, companies, job titles, DOT classifications, physical demand descriptions (postures, positions, lifting, reaching, handling, manipulation, transporting, environmental conditions, sensory conditions), physical demand levels by task, ergonomic risks/opportunities, EHS risks/opportunities, report dates, and evaluations.

In step 15, the report is stored in storage, such as a data repository 103 (FIG. 2). Specifically, a copy of each report is stored with a unique identifier in a Portable Document Format (PDF). This storage allows for later retrieval and future cloning of a report should the need arise. In one embodiment, the storage is cloud based as well known in the art. Likewise, in step 16, the report is integrated for retrial via external systems.

In step 17, the renewal notification is generated. Specifically, each year after the date of purchase of the system, an email notification will be sent to each user or company. This notification is a reminder that the reports completed need to be reviewed. In step 18, the renewal notice is sent. In step 19, if necessary the annual updates of a current or updated report are placed into data storage.

In step 20, the calculated data for Functional Testing Protocol (FTP) is extracted. This process allows the ability to take physical demand data collected and calculated to produce a functional testing protocol for post offer assessment testing and return to work testing. This data is called by external vending systems such as a Functional Capacity Evaluation (FCE) system to allow the two systems to communicate in the same language. This process results in the data for pre-hire post offer testing being specific to the physical demand data and visually captured reporting system. This is a particular advantage of the present invention as the system will be tested and integrated with WorkHab FCE Systems while image captures can now be used for specific task replication in the test development process.

In step 21, the functional testing report is generated. Integration and data extraction make it possible to connect physical demand job criteria and calculated demands directly with a functional capacity reporting system. This process results in accurate testing and reproducibility based on testing protocols and data gathered.

In step 22, the company information is setup. This process establishes company connection with their corresponding data that is collected and analyzed. It allows for reminders, system upgrades, functional test development, annually updating reports, cloning for similar facilities and tasks. The saves time and money for large companies.

In step 23, the company verification of final reports is completed. In this step, the company signs off and verifies each final report as a function of company management and legal liability protection. The signature and review of each final report both initially and annually keeps the company responsible for the information visually documented in each report.

In step 24A, a list of administrative and engineered solutions are created and pulled from a catalog of solutions, wherein the catalog of solution is based on the captured visual images of ergonomic risk/opportunities. These risk solutions provide end users with immediate ways to fix issues either from administrative and engineered controls. Specifically, by pulling through the catalog of solutions, immediate solutions are available without the need to analyze the risk. In step 24B, the catalog of risk solutions is stored in a data repository, such as a data repository 103 (FIG. 2).

In step 25, a clone report process is provided. Specifically, this process allows the user use an existing job or task to expedite the creation of a similar job or task at the same or new company. For instance, the user can clone an existing job, and then the change physical demands and video image captures to a new job. This process is also useful as an edit function.

In step 26, a determination is made if FTP is required. Specifically, the user decides if they want to add FTP regarding the hiring or return to work process. If no, the method is complete. If yes, the process moves to step 27, where the physical demand report data is reviewed for critical demands and essential functions. In this process, the system captures critical physical demands of the existing job. In one embodiment, the weights, frequencies, distances are calculated to establish testing criteria, providing a reliable way to collect and produce baseline testing criteria. In step 28, the previously created testing protocols for use in future testing developments are stored in a database. In step 29, complete test protocols including instructions is used to create a report template. After collection and calculation of physical tests a template is completed to establish a cover sheet of testing with all associated test protocols for printing. In step 30, stored test protocols are added to the final report template, bringing together the templated materials into a single document. These results in a final testing protocol and validity criteria created. The employer can now test employees for the job prior to hire or as a return to work after injury/illness and know that the criteria established to create the test is valid and reliable. This document can be printed in step 31.

In step 32, the testing protocols are verified. Specifically, this additional step is taken by the employer to insure the testing is valid. Workers who currently perform the task are asked to take the functional test to validate the similarity to the work that they currently perform, to determine if the test an accurate representation of the job. If any corrections are necessary, they are corrected in step 33. In step 34, the final version is stored. In step 35, test providers are instructed in the testing process to ensure they trained successfully in protocols for each specific company using the system. In step 36, the testing protocols are available to the test providers. Finally in step 37, verification is provided that the testing protocols are not disqualifying a significant portion of a protected population based on employer results of testing, ensuring that the employer remains in compliance with ADA, EEOC and any pending case law related to testing protocols. If the testing protocols are verified the method is complete. If no, the method returns to step 32.

FIG. 2 is an architectural diagram of an Internet 101 computer network system according to an embodiment of the present invention. The Internet-connected system comprises one or more Internet-connected servers 102 executing the worksite risk analysis and documentation system 100 software from non-transitory media. Server 102 is connected to a data repository 103, which may be any sort of data storage known in the art. The system further comprises a third party Internet-connected server 104 connected to Internet backbone 105. Although one third party Internet-connected server 104 is shown, it is understood that potentially millions of other similar servers are connected to the Internet via Internet backbone 105. A number of users (1-n) 106 are connected to the Internet-connected server via an Internet service provider (ISP) 107, allowing users 106 to access the worksite risk analysis and documentation system.

Server 102 is the centralized computer making the system available to various employers, utilizing the method described herein to analysis and document worksite ergonomic risk/opportunities, health and safety concerns, as well as the physical demands of a job. To avoid workplace injuries, potential lawsuits, negligence, and other issues, the system and method assures a process which is repeatable, trainable, and standardized ensuring compliance and accommodating physical or cognitive deficits for return to work, as well as ADA accommodation strategies, risk reduction, and safety issues.

Figure 3:
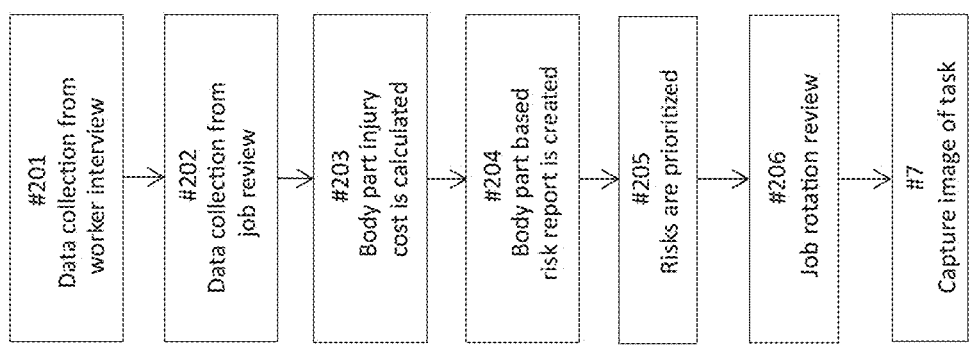
FIG. 3 is a flow diagram showing the steps in a prioritized risk matrix according to an embodiment of the present invention.

FIG. 3 is a flow diagram showing the steps in a prioritized risk matrix. In step 201, data from worker interview about difficulty of job/task is collected. Exemplary data collection step 201 is shown in FIG. 4. In one embodiment, this includes a worker's task name, the frequency of workers time spent on that task, the difficulty of the task, and the reason why that specific task is difficult. In step 202, data from job review, including interview and observational evaluations are collected. Exemplary data collection from step 202 is shown in FIG. 5. In one embodiment, this includes observations for various body parts in "yes" or "no" answers as illustrated. In step 203, body part injury cost is calculated. In one embodiment, the body part injury cost is based on table 1 below.

TABLE 1

| Injury Type | Average Direct Cost ($) |
|---|---|
| Amputation (Hand) | 77,995 |
| Angina Pectoris | 53,461 |
| Asbestosis | 40,037 |
| Asphyxiation | 149,103 |
| Burn | 40,188 |
| Cancer | 129,624 |
| Carpal Tunnel Syndrome | 30,509 |

TABLE 1-continued

| Injury Type | Average Direct Cost ($) |
|---|---|
| Concussion | 59,372 |
| Contagious Disease | 13,364 |
| Contusion | 27,511 |
| Crushing (Hand) | 59,292 |
| Dermatitis | 11,324 |
| Dislocation (Hand) | 74,721 |
| Dust Disease, Noc (All Other Pneumoconiosis) | 31,342 |
| Electric Shock | 93,858 |
| Enucleation (To Remove, Ex: Tumor, Eye, Etc.) | 71,104 |
| Foreign Body | 19,886 |
| Fracture | 50,778 |
| Freezing | 30,564 |
| Hearing Loss Or Impairment (Traumatic Only) | 21,045 |
| Heat Prostration | 23,495 |
| Hernia | 22,313 |
| Infection | 28,301 |
| Inflammation | 36,076 |
| Laceration (Hand) | 19,713 |
| Loss Of Hearing | 17,828 |
| Mental Disorder | 46,214 |
| Mental Stress | 30,947 |
| Multiple Injuries Including Both Physical And Psychological (Hand) | 121,981 |
| Multiple Physical Injuries Only | 73,749 |
| Myocardial Infarction (Heart Attack) | 55,745 |
| No Physical Injury | 24,590 |
| Poisoning - Chemical (Other Than Metals) | 37,565 |
| Poisoning - General (Not Od Or Cumulative Injury) | 31,176 |
| Poisoning - Metal | 15,493 |
| puncture (hand) | 25,523 |
| radiation | 39,493 |
| respiratory disorders (gases, fumes, chemicals, etc.) | 29,137 |
| rupture (back, neck) | 73,057 |
| severance (arm) | 122,091 |
| sprain (all) | 29,989 |
| strain (all) | 33,140 |
| syncope | 34,654 |
| vascular (shoulder) | 141,818 |
| vdt - related disease | 32,488 |
| vision loss | 65,751 |
| all other cumulative injuries, noc | 39,728 |
| all other occupational disease (changed from all other occupational disease or injury | 49,104 |
| all other specific injuries | 43,860 |

Figure 7:
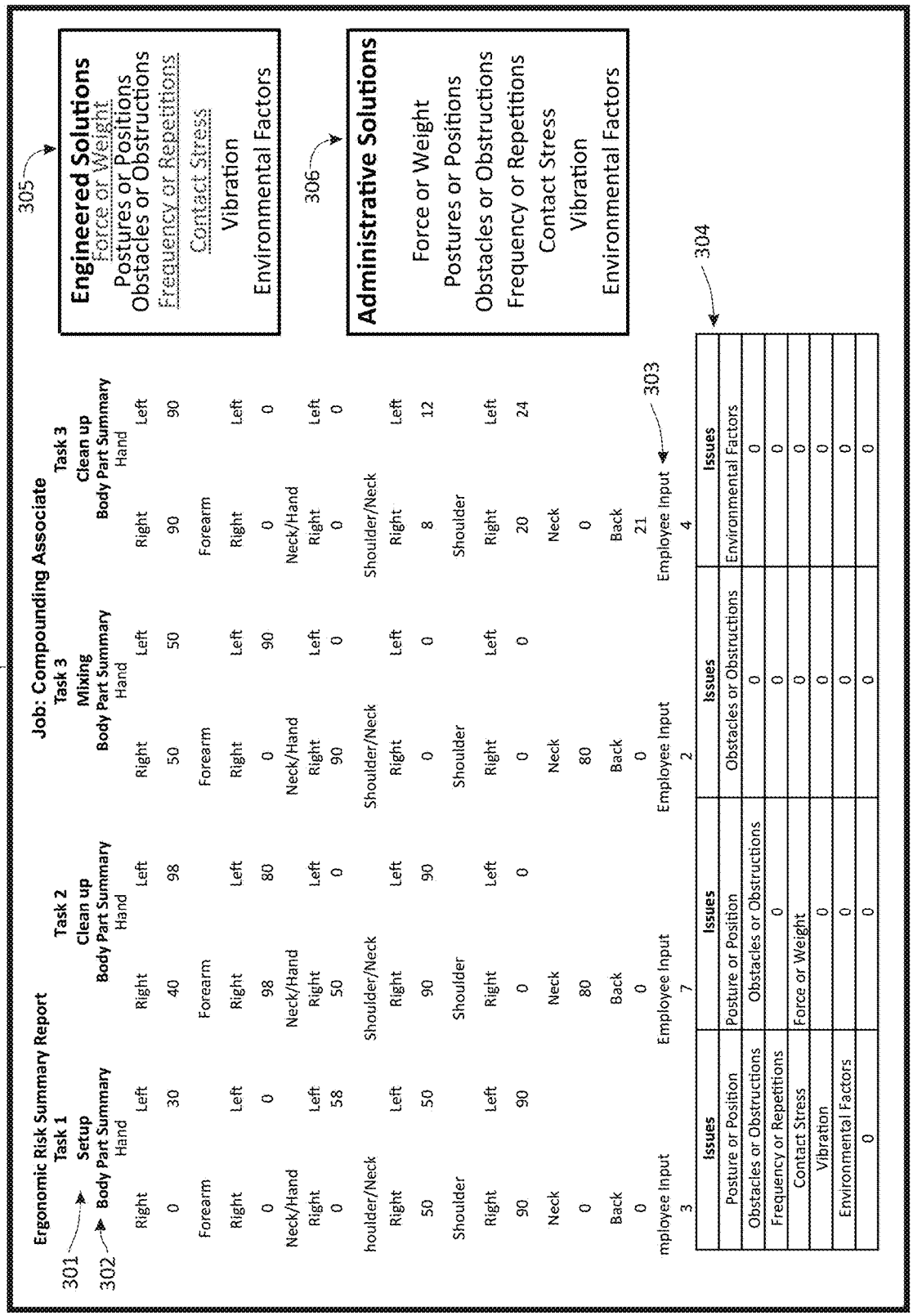
FIG. 7 shows an exemplary report including the solution catalog of engineered and administrative control solutions of FIG. 3.
Figure 11A:
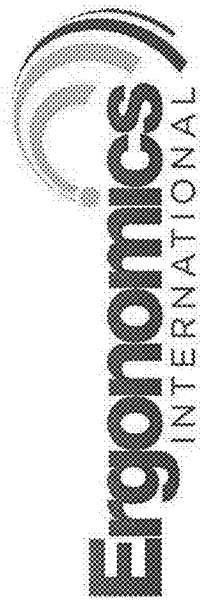
FIGS. 11A-Q show an exemplary physical demand report according to an embodiment of the present invention.
Figure 11B:
Figure 11N:
Figure 110:
Figure 11P:
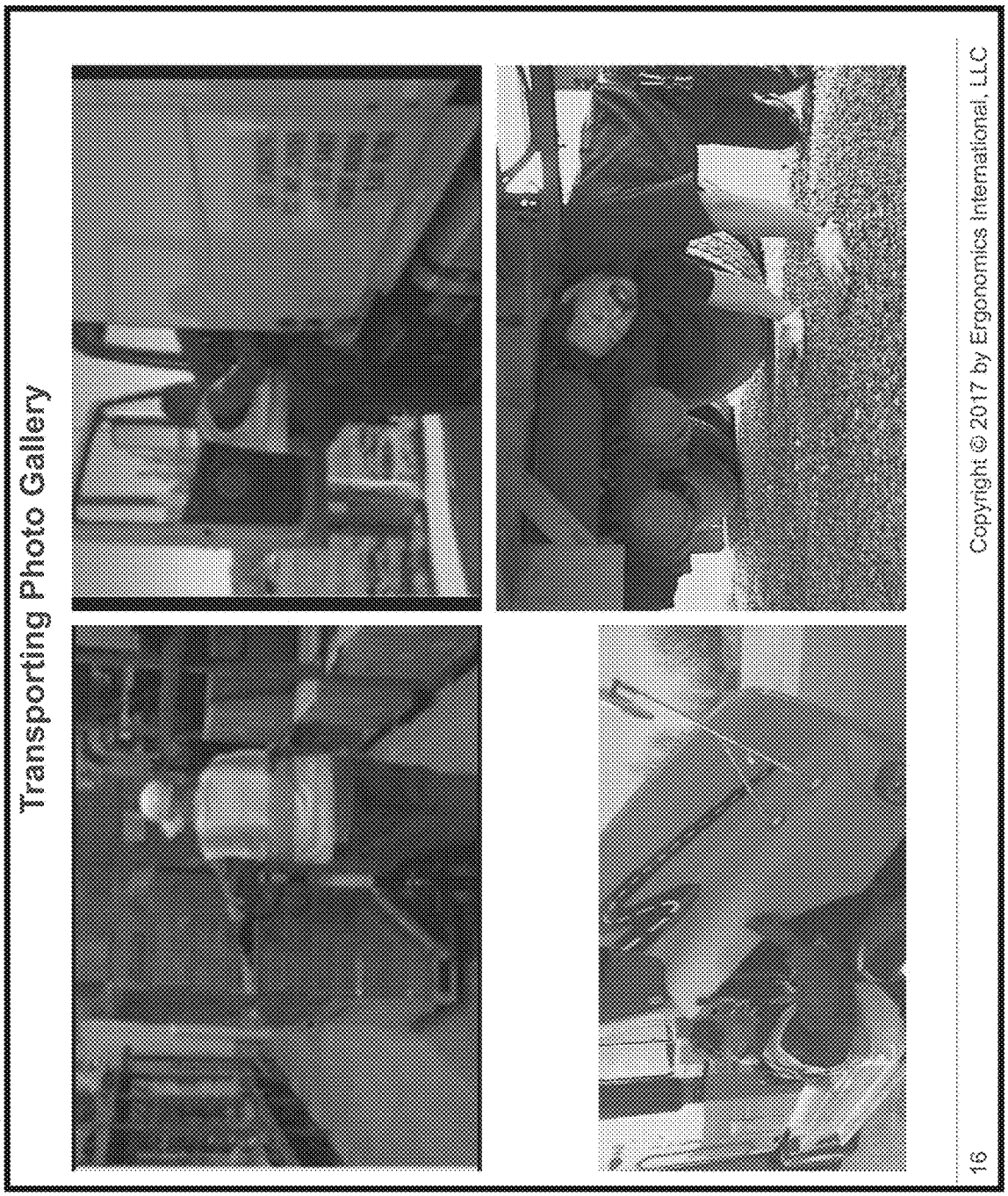
Figure 11Q:

Still Referring to FIG. 3, in step 204, body part based risk report is created. An exemplary body part based risk report is shown in FIG. 6. It should be understood that a body part based risk report of each task of step 201 would be provided. In step 205, risks are prioritized, as described in step 24 of FIG. 1A-C. For instance, with work tasks involving various body parts, each having individual injury costs as indicated in table 1 above, the system will use the higher injury cost to prioritize the risk value. In step 206, observation job/task rotation reviews are provided. In step 207, solution catalog of engineered and administrative control solutions is created. An exemplary report including the solution catalog of engineered and administrative control solutions of step 207 is shown in FIG. 7. Referring now to FIG. 7, the tasks 301 and corresponding exemplary body part summaries 302 are shown, including employee input 303, and potential issues 304. Engineered solutions 305 to the potential issues are provided. For instance, for the issue "contact stress" an engineered solution (product) may be kneepads, elbow pads, wrist support, etc. depending on what the specific job task is (example shown in FIG. 9). In one embodiment, each engineered solution in 305 links, or directs the user to the engineered solutions for each issue. Likewise, administrative solutions 306 are provided for each potential issue.

FIGS. 8A-C show a number of exemplary testing reports generated based on testing protocols (FTP) from the method of FIGS. 1A-C. It should be understood that the exemplary testing reports shown in FIGS. 8A-C, are only a few of possible reports based on a plurality of testing protocols. Each report shows the task specific protocol, including but not limited to test instructions, images related to the test, details related to the test, and an observational review section for the test provider. In one embodiment, the details related to the test include force, repetitions or time requirements, distance, and activities and/or special instructions. For instance, in the "Inclined Surface lift" functional test protocol shown in FIG. 8A, the details include a load force of 20 lbs, having a repetitions requirement of 4 reps per side, and activities and special instructions detail the instructions of the "Inclined Surface lift" test. In some embodiments, the testing protocols include a circuit having a series of tests (as seen in FIG. 8D), as well as the additional details found in FIGS. 8A-C.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

What is claimed is:

1. A system comprising:
    an Internet-connected computerized appliance having a processor and coupled to a data repository, the processor executing software from a non-transitory storage medium, the software providing an interactive interface to a worksite risk analysis and documentation system, the system enabling a user to:
    log on;
    upload video data from a camera or a mobile device;
    capture a plurality of images from the video data to document physical demands and ergonomic risk/opportunities corresponding to a plurality of tasks at a worksite;
    analyze each image of the plurality of images to each task of the plurality of tasks as either a physical demand or an ergonomic risk/opportunity;
    assign each image of plurality of images as either essential or non-essential functions of each task;
    utilize a database of definitions to define and standardize the essential and non-essential functions of each task;
    calculate DOT classification levels to produce a category of work level corresponding to each task for each image categorized as physical demands, wherein the category of work level includes at least one of sedentary work, light work, medium work, heavy work, and very heavy work;
    store the plurality of images in the non-transitory storage medium; and
    generate a final report, wherein the final report includes the plurality of images, the plurality of tasks, the calculated DOT classifications levels, and physical demand descriptions.

2. The system of claim 1, wherein sedentary work is defined as exerting up to 10 pounds of force occasionally to move objects, wherein occasionally is defined as up to one-third of a workday.

3. The system of claim 2, wherein light work is defined as exerting up to 20 pounds of force occasionally and/or up to 10 pounds of force frequently to move objects, wherein frequently is defined between one-third and two-thirds of the workday.

4. The system of claim 3, wherein medium work is defined as exerting 20 to 50 pounds of force occasionally, and/or 10 to 25 pounds of force frequently, and/or up to 10 pounds of force constantly to move objects, wherein constantly is defined as more than two-thirds of the workday.

5. The system of claim 4, wherein heavy work is defined as exerting 50 to 100 pounds of force occasionally, and/or 25 to 50 pounds of force frequently, and/or 10 to 20 pounds of force constantly to move objects.

6. The system of claim 5, wherein very heavy work is defined as exerting in excess of 100 pounds of force occasionally, and/or in excess of 50 pounds of force frequently, and/or in excess of 20 pounds of force constantly to move objects.

7. The system of claim 1, the system further enabling the user to:
create an ergonomic risk/opportunity list, wherein the ergonomic risk opportunity list includes a priority ranking for each observation corresponding to each image of the plurality of images to each task of the plurality of tasks analyzed as an ergonomic risk/opportunity, a description of the ergonomic opportunity/risk, and a recommendation to improve the ergonomic opportunity risk.

8. The system of claim 1, the system further enabling the user to:
identity specific body parts affected by the physical demands.

9. The system of claim 8, the system further enabling the user to:
create a body part based risk report for each task of the plurality of tasks including at least one body part, wherein each body part of the at least one body part having an individual injury cost, such that the system is configured to prioritize a risk value for each body part of the at least one body part.

10. The system of claim 9, the system further enabling the user to:
create a report, wherein the report includes a solution catalog of engineered solutions and administrative control solutions for the body part based risk report.

11. The system of claim 10, wherein the solution catalog of engineered solutions provides a list of products configured to help reduce injury to each body part.

12. A method comprising steps:
(a) providing training and credentialing of a plurality of users for use of a worksite risk analysis and documentation system;
(b) recording video data via a camera or a mobile device at a worksite;
(c) enabling a user of the plurality of users to access the worksite risk analysis and documentation system from a geographical location via an Internet connection;
(d) enabling the user to upload the video;
(e) capturing a plurality of images from the video data to document physical demands and ergonomic risk/opportunities corresponding to a plurality of tasks at the worksite;
(f) analyzing each image of the plurality of images to each task of the plurality of tasks as either a physical demand or an ergonomic risk/opportunity;
(g) assigning each image of plurality of images as either essential or non-essential functions of each task;
(h) accessing a database of definitions to define and standardize the essential and non-essential functions of each task;
(i) calculating DOT classification levels to produce a category of work level corresponding to each task for each image categorized as physical demands, wherein the category of work level includes at least one of sedentary work, light work, medium work, heavy work, and very heavy work;
(j) storing the plurality of images in the non-transitory storage medium; and
(k) generating a final report, wherein the final report includes the plurality of images, the plurality of tasks, the calculated DOT classifications levels, and physical demand descriptions.

13. The method of claim 12, further comprising a step of creating an ergonomic risk/opportunity list, wherein the ergonomic risk opportunity list includes a priority ranking for each observation corresponding to each image of the plurality of images to each task of the plurality of tasks analyzed as an ergonomic risk/opportunity, a description of the ergonomic opportunity/risk, and a recommendation to improve the ergonomic opportunity risk.

14. The method of claim 12, further comprising a step of identifying specific body parts affected by the physical demands.

15. The method of claim 14, further comprising a step of creating a body part based risk report for each task of the plurality of tasks including at least one body part, wherein each body part of the at least one body part having an individual injury cost, such that the system is configured to prioritize a risk value for each body part of the at least one body part.

16. The method of claim 15, further comprising a step of creating a report, wherein the report includes a solution catalog of engineered solutions and administrative control solutions for the body part based risk report.

17. The method of claim 16, wherein the solution catalog of engineered solutions provides a list of products configured to help reduce injury to each body part.

* * * * *